United States Patent [19]

Scates et al.

[11] Patent Number: 5,599,976
[45] Date of Patent: Feb. 4, 1997

[54] RECOVERY OF ACETIC ACID FROM DILUTE AQUEOUS STREAMS FORMED DURING A CARBONYLATION PROCESS

[75] Inventors: Mark O. Scates, Friendswood; Steven E. Parker, Seabrook; Jennifer B. Lacy; Russell K. Gibbs, both of Houston, all of Tex.

[73] Assignee: Hoechst Celanese Corporation, Sommervile, N.J.

[21] Appl. No.: 418,333

[22] Filed: Apr. 7, 1995

[51] Int. Cl.⁶ .................................................. C07C 51/12
[52] U.S. Cl. ................................................................ 562/519
[58] Field of Search ............................................ 562/519

[56] References Cited

U.S. PATENT DOCUMENTS

| | | | |
|---|---|---|---|
| 3,278,585 | 10/1966 | Baker et al. ............................ | 260/473 |
| 4,234,719 | 11/1980 | Wan ......................................... | 536/69 |
| 4,435,595 | 3/1984 | Agreda et al. .......................... | 560/234 |
| 5,371,286 | 12/1994 | Blay et al. .............................. | 562/519 |

*Primary Examiner*—Porfirio Nazario-Gonzalez
*Assistant Examiner*—Rosalynd Williams
*Attorney, Agent, or Firm*—Donald R. Cassady; Stuart D. Frenkel

[57] ABSTRACT

A method is provided to improve the quality of recycle of certain residues by modifying the separation of alkanes and alkane-like materials and carbonyl-containing impurities from the recycle during the manufacture of acetic acid by the carbonylation of methanol. The improvement comprises partitioning the residues by the addition of water obtained from aqueous streams containing up to 50 wt. % acetic acid and which have been treated in a catalytic distillation unit to react the acetic acid with methanol to form recyclable methyl acetate and water and wherein the water is separated from the organics by distillation.

8 Claims, 2 Drawing Sheets

RECOVERY OF ACETIC ACID FROM DILUTE AQUEOUS STREAMS FORMED DURING A CARBONYLATION PROCESS

BACKGROUND OF THE INVENTION

This invention relates to a novel process for the recovery of acetic acid from dilute aqueous streams. In particular, this invention relates to such recovery from dilute aqueous streams which have been formed during the carbonylation of methanol or methyl acetate in the presence of a Group VIII metal carbonylation catalyst to acetic acid and to the purification thereof. More specifically, this invention pertains to a novel process for separating acetic acid from dilute aqueous streams and using the purified aqueous stream in acetic acid purification such as for removing alkane impurities from an acetic acid product formed by Group VIII metal catalyzed carbonylation processes.

Among currently-employed processes for synthesizing acetic acid, one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium, or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. Most typically and usefully, the reaction is conducted with the catalyst being dissolved in a liquid reaction medium through which carbon monoxide gas is continuously bubbled.

An improvement in the prior-art process for the carbonylation of an alcohol to produce the carboxylic acid having one carbon atom more than the alcohol in the presence of a rhodium catalyst is disclosed in commonly assigned U.S. Pat. No. 5,001,259, issued Jun. 25, 1991, and European patent application 161,874; published Nov. 21, 1985. As disclosed therein acetic acid is produced from methanol in a reaction medium comprising methyl acetate, methyl halide, especially methyl iodide, and rhodium present in a catalytically-effective concentration. The invention therein resides primarily in the discovery that catalyst stability and the productivity of the carbonylation reactor can be maintained at surprisingly high levels, even at very low water concentrations, i.e. 12 wt. % or less, in the reaction medium (despite the general industrial practice of maintaining approximately 14 wt. % or 15 wt. % water) by maintaining in the reaction medium, along with a catalytically-effective amount of rhodium, at least a finite concentration of water, methyl acetate, and methyl iodide, a specified concentration of iodide ions over and above the iodide content which is present as methyl iodide or other organic iodide. The iodide ion is present as a simple salt, with lithium iodide being preferred. These patent publications teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can broadly be defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Pat. No. 5,001,259 is herein incorporated by reference.

The acetic acid which is formed by the carbonylation of methanol is converted to a high purity product by conventional means such as by a series of distillations. During the distillations to purify the acetic acid product, there are obtained aqueous streams which contain minor amounts of acetic acid, organic iodide co-catalyst and methyl acetate which are recycled to the carbonylation reactor. Since it is advantageous at least as far as increasing production of acetic acid to reduce the water content in the carbonylation reactor to well below 12% and, preferably, approach 3–4 wt. % water in the carbonylation reactor, the recycle of these aqueous streams from the purification process renders the management of the water level in the reactor problematic. It is not efficient to simply discard these aqueous streams since valuable acetic acid product would be discarded as well as necessary reactants which would have to be made up by new and more expensive supplies.

During the purification of the acetic acid formed by the above-mentioned carbonylation, it is known to utilize aqueous streams to aid in the removal of impurities from the acetic acid product. Thus, it has been found that under the low water carbonylation conditions the acetic acid which is produced under such conditions is deficient in permanganate time. Among the impurities which degrade permanganate time of the acetic acid are carbonyls and organic iodides. In EPO Published Application 487,284, published May 5, 1992, is disclosed a process to minimize the amount of circulating carbonyl-containing and unsaturated organic materials in the carbonylation reaction mixture resulting in a more facile purification of acetic acid. By such process, the carbonyl impurities are reacted with an amine compound to form oximes wherein the oximes are removed by distillation including the addition of water to extract or otherwise solvate the oximes in an aqueous phase.

Another purification process which involves the removal of impurities from the acetic acid product involves the removal of alkanes from the crude acetic acid product. The formation of alkanes was recognized by Price. His invention, described and claimed in U.S. Pat. No. 4,102,922, involved removing the alkanes by stripping the volitile components of the reaction away from the alkanes after removal of the catalyst. The reaction mixture is carried to a pressure let-down vessel denoted as a flasher where the products are vaporized and removed from a residue of catalyst. The catalyst is recycled to the reactor. The flashed product containing methyl iodide, water, acetic acid, and the alkanes is fed to a splitter and allowed to separate into at least two liquid phases, one phase containing acetic acid and water which is returned to the reactor and a second phase denoted herewithin as a heavy phase. To effect removal of the alkanes, a slipstream of the heavy phase from the splitter column is stripped using carbon monoxide as a stripping gas, removing the alkanes as the bottoms stream from the latter distillation.

Disclosed in commonly assigned U.S. Pat. No. 5,371,286, is a method by which the alkanes are removed according to the method of Price but with the unexpected benefit of realizing the recovery of acetic acid from the residue that would normally be discarded by the practice of the prior art. In a preferred embodiment of the invention, a method is provided for effecting the alkanes removal at low-water conditions wherein the water balance in the reaction system is maintained.

As disclosed therein, the carbonylation of methanol, dimethyl ether, methyl acetate, or a mixture thereof takes place in the presence of a Group VIII metal carbonylation catalyst. Such carbonylation reactions comprise catalytic reaction with carbon monoxide in the presence of a halide promoter such as an organic halide as disclosed in U.S. Pat. No. 3,769,329 or under low water conditions such as disclosed in aforementioned U.S. Pat. No. 5,001,259 wherein the catalyst solution contains not only the Group VIII metal catalyst and organic halide promoter, but also contains an additional iodide salt. In such processes, a feed of methanol, dimethyl ether, methyl acetate, or mixture thereof is carbonylated in a liquid phase carbonylation reactor. Separation of products is achieved by directing the contents of the reactor to a flasher wherein the catalyst solution is withdrawn as a base stream and recycled to the reactor while the overhead which comprises largely the product acetic acid along with methyl iodide, methyl acetate, and water is directed to a methyl iodide-acetic acid splitter column. The overhead from the splitter column comprises mainly organic iodides and methyl acetate whereas from the base or side stream of the splitter column is drawn the acetic acid product which is usually directed to further purification by finishing distillation. It is a portion of the overhead, heavy phase, that contains a majority of the alkanes which are removed by the process of the invention disclosed therein. Thus, the heavy phase from the splitter column overhead is distilled in a refluxing column at a reflux ratio of from about 0.5 to about 5. The overhead from this refluxing column, containing methyl iodide, methyl acetate, and carbonyl impurities, is removed and returned to the reactor or treated further to remove the carbonyl impurities. The residue from this column is passed to a decanter where the phases are caused to separate by the addition of water. The bottom phase being substantially water and acetic acid is returned to the reactor. The upper phase being substantially all of the alkanes is waste and can be used as feed to an incinerator or the like for disposal. In a preferred embodiment of the invention disclosed in U.S. Ser. No. 052,429, the phases are caused to separate by the addition of a slipstream of the overhead from the acetic acid drying column further down in the purification train. The drying column overhead is first distilled to separate a methyl acetate and methyl iodide distillate from the aqueous bottoms. The aqueous bottoms derived from distilling the drying column overhead is used to provide water for the phase separation and some water balance in the carbonylation reaction system.

Unfortunately, the slipstream from the drying column overhead which is utilized can contain up to 20 wt. % acetic acid which remains in the aqueous bottom phase during distillation to remove the methyl acetate and methyl iodide. Removal of the acetic acid from this stream will make it much more effective in the phase separation of the alkanes from the aqueous phase. Moreover, if too much water is present in the system, purging the aqueous stream without effectively removing acetic acid product therefrom is not efficient as valuable acetic acid product is discarded. Methods of separating the acetic acid from the aqueous phase such as by distillation or solvent extraction are not cost effective in view of the energy costs involved in the distillation process and the need for high capital investment if solvent extraction is utilized.

Accordingly, there is a need to control the water levels in the carbonylation system, in particular, when the water concentration in the carbonylation reactor is to be maintained below about 12 wt. %.

Further, there is a need to treat other dilute acid aqueous streams in the carbonylation separation and purification process to separate the acetic acid from the aqueous phase in a cost efficient manner. As for example, the light phase from the stripper column contains acetic acid and water which can be used to cause the phase separation described above were the acetic acid and water separated. The water recycle could then be more easily controlled without the concommitant loss of acetic acid.

As the concentration of water in the reactor is lowered to less than 12 weight percent range the inventors have found that there are additional needs to treat dilute acid aqueous streams in the purification process to separate the acetic acid from dilute aqueous solutions to avoid discarding any acetic acid product with the water and provide a more controlled, purified aqueous stream which can be recycled or used effectively during purification of the acetic acid product.

SUMMARY OF THE INVENTION

The process of the present invention is directed to the treatment of dilute acetic acid aqueous streams which are formed during the carbonylation of methanol, dimethylether, methyl acetate or mixtures thereof in the presence of a group VIII metal carbonylation catalyst and, in particular, to the treatment of such streams so as to effectively and cost efficiently separate the acetic acid from the aqueous phase. Separation of the acetic acid from the aqueous phase allows the aqueous phase to be used in the purification of the acetic acid such as for the removal of carbonyls as described in EPO published application 487,284 and/or removal of alkanes as described in U.S. Pat. No. 5,371,286. Also, importantly, the aqueous streams which are now freed from the relatively minor amounts of acetic acid contained therein can be recycled as needed or purged without discarding valuable product, thus providing an improved method of controlling the water content throughout the carbonylation process. This is particularly useful if the water content in the carbonylation reactor is greatly reduced such as to below 12 and even to below 5 wt. %. Previous processes which recycled the aqueous streams containing the reactants, cocatalysts and acetic acid added the water to the inventory of the reactor. These streams could not be readily discarded due to the costs of discarding the valuable starting materials and acetic acid product present in the aqueous streams.

Thus, in accordance with the present invention, dilute aqueous acid streams from the acetic acid purification process, as for example the dilute acid light phase from the splitter column, and/or at least a slip stream from the overhead of the acetic acid drying column and which contains water and minor amounts of acetic acid, methyl iodide, and methyl acetate is treated by the addition of methanol under conditions which cause the methanol to react with the acetic acid to form lower boiling methyl acetate and water and wherein the methyl acetate, methyl iodide, and any unreacted methanol are separated from the aqueous phase by distillation.

The treatment of the drying column overhead is accomplished by catalytic distillation in the presence of an acid catalyst. Fed into the catalytic region of the catalytic distillation unit are the overhead from the drying column and methanol. The formed methyl acetate is removed as distillate from the unit and the purified water phase is removed as a bottoms product from the unit. It has been found that at least about 90% of the acetic acid in the drying column overhead can be converted to methyl acetate and removed as distillate which is then recycled into the carbonylation process. The bottoms water phase can be used to aid in the separation of the alkanes and/or carbonyls from acetic acid product as previously described. If desired, for water balance purposes, a portion of the bottoms water phase can be purged without discarding valuable commodities. Additionally, the extraction efficiency during the phase separation of the alkanes and/or carbonyls from the acetic acid can be substantially improved reducing the volume of waste.

DETAILED DESCRIPTION OF THE INVENTION

The process for treating dilute acetic acid aqueous streams in accordance with this invention can be described in conjunction with the purification process for recovering a pure acetic acid product formed by carbonylation. In particular, the separation of alkanes from the acetic acid product can have usefully incorporated therein the treatment process of this invention.

The purification process of the present invention is useful in any process used to carbonylate methanol, dimethyl ether, methyl acetate, and mixtures thereof to acetic acid in the presence of a Group VIII metal catalyst such as rhodium and an iodide promoter. A particularly useful process is the low-water rhodium catalyzed carbonylation of methanol to acetic acid as exemplified in aforementioned U.S. Pat. No. 5,001,259. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing rhodium into the reaction zone wherein the rhodium is in the form of rhodium metal, rhodium salts and oxides, organic rhodium compounds, coordination compounds of rhodium, and the like.

The halogen-containing promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl portion corresponds to the alkyl portion of the feed alcohol which is carbonylated. Thus, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

It is known that in rhodium-catalyzed carbonylation reactions of the type set forth in this invention, the addition of water exerts a beneficial effect upon the reaction rate (U.S. Pat. No. 3,769,329). Thus, commercial operations run at water concentrations of at least 14 wt. % (EP 055618). Accordingly, it is quite unexpected that reaction rates substantially equal to and above reaction rates obtained with such high levels of water concentration can be achieved with water concentrations below 14 wt. % and as low as 0.1 wt. %.

In accordance with the carbonylation process most useful to manufacture acetic acid, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously. Iodide ion concentrations as high as 2–20 wt. % may be useful to stabilize the catalyst and promote the reaction. This had not been recognized in the prior art previous to disclosure in U.S. Pat. No. 5,001,259. The concentration of lithium iodide used in the reaction medium of the preferred carbonylation reaction system is believed to be quite high as compared with what little prior art there is dealing with the use of halide salts in reaction systems of this sort.

The carbonylation reaction of methanol to acetic acid product may be carried out by intimately contacting the methanol feed, which is in the liquid phase, with gaseous carbon monoxide bubbled through a liquid reaction medium containing the rhodium catalyst, methyl iodide promoting component, methyl acetate, and additional soluble iodide salt promoter, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation. Preferably it is an iodide salt of a member of the group consisting of the metals of Group Ia and Group IIa of the periodic table as set forth in the "Handbook of Chemistry and Physics" published by CRC Press, Cleveland, Ohio, 1975–76 (56th edition). In particular, alkali metal iodides are useful, with lithium iodide being preferred. In the low water carbonylation most useful in this invention, the additional iodide over and above the organic iodide promoter is present in the catalyst solution in amounts of from about 2 to about 20 wt. %, preferably 5–15 wt. %, the methyl acetate is present in amounts of from about 0.5 to about 30 wt. %, preferably 2–5 wt. %, and the methyl iodide is present in amounts of from about 5 to about 20 wt. %, preferably 10–16 wt. %, and most preferably 12–15 wt. %. The rhodium catalyst is present in amounts of from 200–1000 and preferably 300–600 ppm.

Typical reaction temperatures for carbonylation will be approximately 150°–250° C., with the temperature range of about 180°–220° C. being the preferred range. The carbon monoxide partial pressure in the reactor can vary widely but is typically about 2–30 atmospheres, and preferably, about 3–10 atmospheres. Because of the partial pressure of by-products and the vapor pressure of the contained liquids, the total reactor pressure will range from about 15 to 40 atmospheres.

Figure 1:
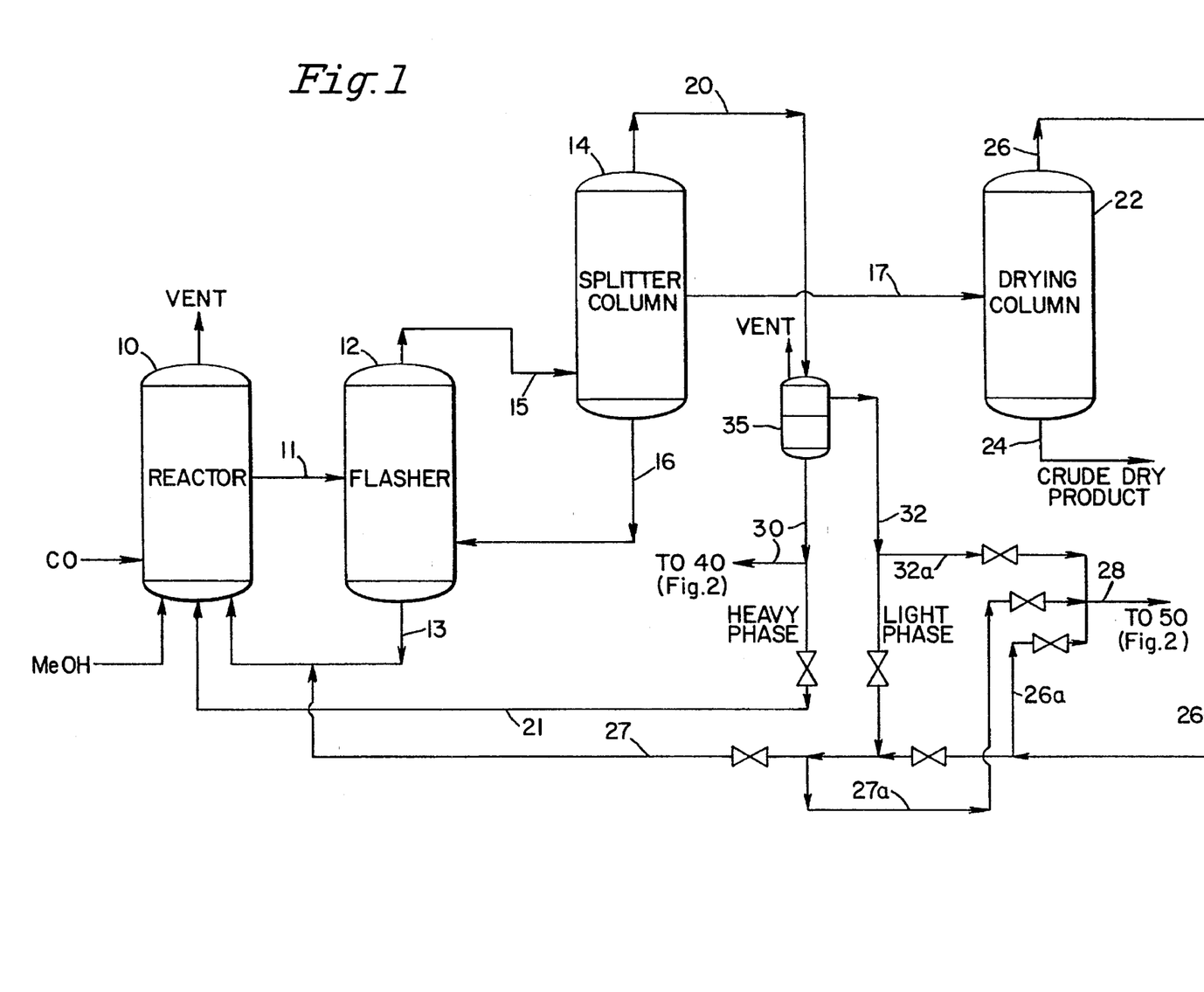
FIG. 1 represents a typical acetic acid reaction and recovery system adapted to be connected to the alkanes recovery system of this invention.

A typical reaction and acetic acid recovery system which may be used for the iodide-promoted rhodium catalyzed carbonylation of methanol to acetic acid is shown in FIG. 1 and comprises a liquid-phase carbonylation reactor 10, flasher 12, a methyl iodide-acetic acid splitter column 14 and an acetic acid drying column 22. The carbonylation reactor 10 is typically a stirred vessel within which the reacting liquid contents are maintained automatically at a constant level. Into this reactor there are continuously introduced fresh methanol, sufficient water as needed to maintain at least a finite concentration of water in the reaction medium, recycled catalyst solution from the flasher base, a recycled methyl iodide and methyl acetate phase, and an aqueous acetic acid phase from the overhead of the methyl iodide-acetic acid splitter column 14. Alternate distillation systems can be employed so long as they provide means for recovering the crude acetic acid and recycling catalyst solution, methyl iodide, and methyl acetate to the reactor. In a preferred process, carbon monoxide is continuously introduced into the carbonylation reactor 10 just below the agitator which is used to stir the contents. The gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from carbonylation reactor 10 at a rate sufficient to maintain a constant level therein and is introduced to flasher 12 via line 11. In flasher 12 the catalyst solution is withdrawn as a base stream 13 (predominantly acetic acid containing the rhodium and the iodide salt along with lesser quantities of methyl acetate, methyl iodide, and water), while the overhead 15 of the flasher comprises largely the product acetic acid along with methyl iodide, methyl acetate, and water. Dissolved gases in stream 11 consisting of a portion of the carbon monoxide along with gaseous by-products such as methane, hydrogen, and carbon dioxide, exit the flasher through stream 15 to the splitter column 14 thence to the splitter column overhead receiver 35, and exit the system through a vent on the top of the splitter column overhead receiver 35. The overhead 20 from methyl iodide-acetic acid spitter, comprising mainly methyl iodide and methyl acetate plus some water, acetic acid and volatiles, is normally recycled via line 21 to the carbonylation reactor 10.

The product acetic acid drawn from the side of methyl iodide-acetic acid spitter column 14 near the base (it can also be withdrawn as a base stream) is directed via line 17 to drying column 22 for final purification such as to remove water by distillation.

In accordance with the carbonylation process of Price, loc cit, it has been found that the alkane impurities which accumulate in the overhead 20 are removed from this stream to prevent a substantial build-up of alkanes in the reactor thus providing an improvement in acetic acid product quality. According to Price, alkane removal is accomplished by the stripping of the material from stream 30 with a stream of carbon monoxide. The residue from this process separates into two phases upon cooling as has been shown in the Comparative Example below. The uppermost layer contains alkanes and alkyl iodides, while the lowermost layer contains predominately the acetic acid, propionic acid, and water.

When overhead 20 is condensed according to the method of this invention it typically splits into two liquid phases in decanter 35 if sufficient water is present. The heavy phase 30 is comprised mainly of methyl iodide plus some methyl acetate and acetic acid as well as the alkane and carbonyl impurities. The light phase 32 is comprised mainly of water and acetic acid plus some methyl acetate and carbonyl impurities. The heavy phase 30 from the methyl iodide-acetic acid splitter is subject to treatment according to this invention as stream 40, or is recycled as stream 21.

Figure 2:
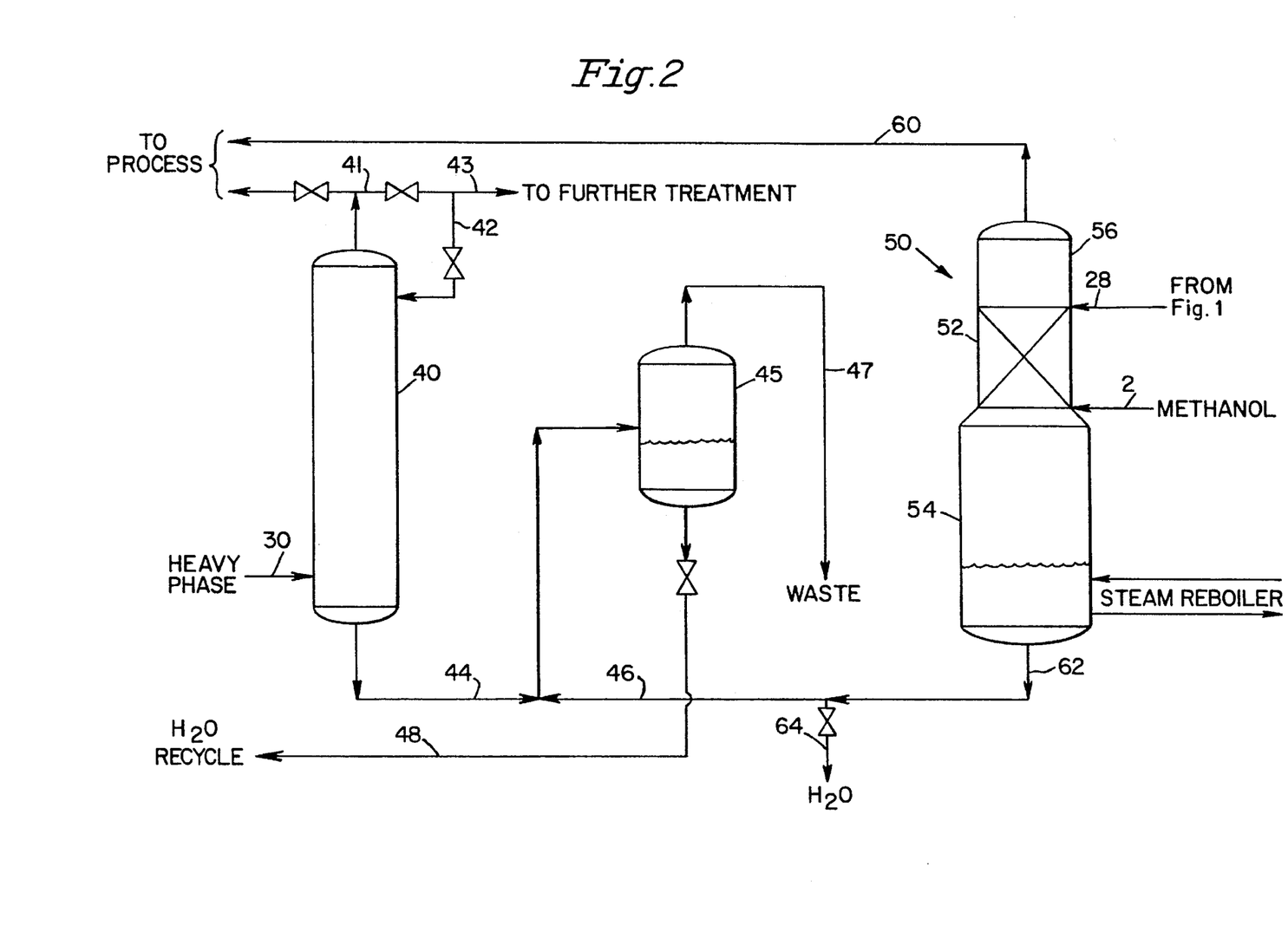
FIG. 2 represents the alkanes recovery system of this invention.

As discussed above we have found that separation of stream 20 into a heavy phase 30 and a light phase 32 in decanter 35, allows the light phase to be used to feed a catalytic distillation system 50 and the heavy phase to be distilled in a simple distillation in a reflux column wherein the reflux ratio is from about 0.5 to about 5, preferably from about 1 to about 3, and the bottoms from the column passed to a decanter 45. Addition of water to the decanter 45 from the stripping section 54 of the catalytic distillation column 50 causes the bottoms, which normally do not separate into two phases, to separate into the two phases, and the separation proceeds with more of the alkanes partitioning into the upper layer and more of the acids partitioning into the aqueous lower layer than that shown by our comparison with the Price method. This enhanced separation provides a lowermost aqueous phase which contains additional recoverable acetic acid. This acetic acid can most advantageously be recycled to the process instead of being lost to the system according to the Price method.

In accordance with the treatment process of this invention, the water for the separation may be derived from various streams in the purification process, as more particularly from the acetic acid drying column 22 or splitter column 14. According to the invention, at least a slipstream from the overhead 26 of drying column 22, and/or light phase 32 from the splitter column 14, and containing predominately water, plus some acetic acid, methyl iodide, and methyl acetate is reacted with methanol to convert the acetic acid to methyl acetate and water and the light organic components including methyl iodide, methyl acetate, and unreacted methanol are recycled to the process leaving the water which is then used to cause the separation in vessel 45 of the bottoms from tower 40. The overhead 26 from drying column 22 typically contains 5–20 wt. % acetic acid. The light phase from the splitter column 14 typically contains 20–30 wt. % acetic acid. In the process disclosed in aforementioned U.S. Pat. No. 5,371,429, the overhead 26 is distilled to remove methyl iodide and methyl acetate from the aqueous phase containing the acetic acid. The dilute acetic acid aqueous phase is used in the separation. As before stated, alkane removal is not substantially improved if the higher levels of acetic acid are present. Likewise, purging the aqueous stream is not very cost efficient, since acetic acid is being discarded.

In the first stage of the alkane removal process as shown in FIG. 2, the heavy phase stream 30, which contains the alkane and carbonyl impurities, enters into reflux column 40 in which a reflux ratio of from about 1 to about 50 is maintained through streams 42 and 43. The overhead stream is either recycled to the process or treated further to remove the carbonyl impurities, as for example according to the method of co-pending application our Docket c-7046 or EPO published application 487,284 prior to being recycled.

The residue from column 40, as stream 44, enters decanter 45. An aqueous stream 46 is also added to the decanter through stream 44 causing separation of the residue into two phases. The upper organic phase as stream 47 contains the alkanes which are disposed of in an environmentally sound manner and the lower aqueous phase as stream 48 contains the water and acetic acid which either is recycled to the reactor 10, the flasher 12, the splitter column 14, the drying column 22, or the decanter 35.

In accordance with the present invention, at least some, if not all, of the aqueous stream 46 directed to decanter 45 to separate the alkanes from the aqueous phase is derived from the aqueous overhead 26 from drying column 22. Referring now to FIG. 2, the treatment of the drying column overhead 26 to react and separate the acetic acid (as methyl acetate) from the water can be described in more detail. The overhead 26 or a slipstream therefrom is directed to a catalytic distillation unit 50 wherein upon the addition of methanol (MeOH), the acetic acid (HAc) is esterified in the presence of an acid catalyst to produce methyl acetate (MeAc) and water as follows:

In the reaction, in accordance with the process of the present invention, methanol and acetic acid are reacted in a single continuous catalytic distillation unit 50 which provides sufficient residence time to achieve high conversion of the reactants to methyl acetate product. It has been found that greater than 90% of the acetic acid contained in drying column overhead 26 can be converted to methyl acetate.

The high conversions of methanol and acetic acid to methyl acetate are achieved by the counter-current flow of reactants and simultaneous removal of products. Referring again to FIG. 2, the drying column overhead 26 containing water, from about 5–20 wt. % acetic acid and minor amounts of methyl iodide and methyl acetate is fed to the top of catalytic region 52 positioned in unit 50 while methanol is fed to the bottom of catalytic region 52. The conditions throughout unit 50 are such that the reactants flow counter-currently through catalytic region 52 and react to form methyl acetate and water. The methyl acetate having a lower boiling point than the water is distilled overhead and can be returned to the carbonylation system. The bulk of the water which is formed is directed downwardly through unit 50 and forms a residue stream which is directed from the bottom of unit 52 as aqueous stream 62, all or part of which can form aqueous stream 46.

The esterification of acetic acid with methanol is an equilibrium reaction in which the reverse reaction comprising the hydrolysis of methyl acetate to yield the methanol and acetic acid reactants will normally take place under batch conditions. By continually reacting methanol with the acetic acid contained in the drying column overhead 26, and/or splitter column light phase 32, and distilling off the methyl acetate which is formed, the reaction is driven to the formation of methyl acetate and water and provides for a high purity aqueous bottom stream leaving unit 50.

A more detailed description of catalytic distillation unit 50 and conditions therein can now be provided. Feed stream 28 to the unit is comprised of various dilute acetic acid streams from the unit, particularly, stream 32a, a slip stream from stream 32 which is comprised of the light phase from the splitter column decanter 35, stream 26a, a slip stream from stream 26, the drying column overhead, and, 27a, a slip stream from the combination of the drying column overhead and the light phase from the splitter column decanter 35. The catalytic distillation unit 50 is configured and operated so as to provide intimate contact in the unit between the acetic acid and methanol reactants and between the acetic acid and methanol reactants with the catalyst. The catalyst which is utilized is preferably a strong acid catalyst. Preferably the catalyst is used in the solid form as a fixed bed which is held in unit 50 by trays or packing. The acid catalyst is preferably a cationic ion exchange resin containing sulfonic acid groups. Amberlyst 15®, Amberlyst 35® and Amberlyst 36® have been found particularly useful in catalyzing the reaction of the methanol with the acetic acid contained in the drying column overhead 26 and/or the light phase stream 32. The fixed bed of catalyst forms catalytic region 52. While it is possible to provide the catalyst as a liquid such as sulfuric acid, it would be necessary to separate the catalyst from the aqueous bottoms before use in the alkane separation. In the preferred fixed bed configuration, any tray or packing design which is known to hold a fixed bed catalyst is applicable for use in the catalytic distillation unit 50 of the present invention. A particular useful means to hold the fixed bed catalyst in unit 50 is Koch Katamax® packing.

The methanol reactant can be provided to unit 50 in approximately stoichiometric quantities relative to the acetic acid contained in the ingress stream 28. The methanol to acetic acid mole ratio should be at least 1:1 to insure that substantially all of the acetic acid is converted to methyl acetate. Excesses of methanol are preferred. There is no particular maximum excess of methanol to be provided inasmuch as any excess methanol is simply distilled from unit 50 and returned as reactor feed to the carbonylation reactor 10 via line 60 overhead of unit 50. Generally, however, methanol to acetic acid mole ratios should range from about 1:1 to about 10:1, preferably, from about 2:1 to 5:1 and, most preferably, from about 3:1 to 5:1.

Below catalytic region 52 in unit 50 is a methanol stripping section 54. Stripping section 54 is operated so as to separate the lower boiling methyl acetate and methanol from the higher boiling water and acetic acid which falls to the bottom of the unit 50. The bottom stripping section 54 of unit 50 is typically heated to the appropriate temperature relative to pressure conditions by steam so as to distill the methanol from the water. As the methanol rises, this reactant contacts the catalytic region 52 and the counter-currently flowing acetic acid to react to form methyl acetate and water.

Stripping section 54 can comprise any of the conventional distillation trays which are adapted for counter-current vapor-liquid contacting and include sieve trays, bubble cap trays, valve trays, tunnel cap trays and the like. In addition, the stripping section 54 can comprise inert packings including bed saddles, rashig rings, interlock saddles, various structured packings and the like. Both distillation trays and packed sections can be employed in stripping section 54.

Region 56 above catalytic region 52 in catalytic distillation unit 50 can be configured in an alternative manner. In one configuration, region 56 is a rectifying section, preferably operated in a reflux mode, in which conventional distillation trays or packing as described immediately above are incorporated in the section so as to improve the separation of the formed methyl acetate and other low boiling organics such as methyl iodide and methanol from water. The methyl acetate, methyl iodide and unreacted methanol are distilled overhead of unit 50 via line 60 for recycle to the carbonylation process. The water which remains in column 50 passes down through the column to form part of the residue stream 62. The rectifying section can be operated with or without reflux. The use of a rectifying section in region 56 of unit 50 is optional but has been found to greatly reduce the amount of water distilled from the top of unit 50 and likewise, decreases the percentage of acetic acid which remains in the aqueous bottoms stream. On the other hand, without rectification, the concentration of water contained in the distillate from unit 50 via line 60 is substantially greater than when rectification is utilized. However, the overall mass flow of water that distills in overhead line 60 is substantially less than the mass flow of water fed to unit 50 and present in the drying column overhead 26 or light phase stream 32. Thus, if the distillate from unit 50 is all recycled to the reactor 10, the mass flow of water present in stream 60 is substantially less than the mass flow in stream 26 or 32, thereby allowing water to be purged from the system, even though the distillate 60 contains up to about 40 wt. % water.

The bottoms or aqueous residue stream 62 which contains 2 wt. % or less of the acetic acid which was fed to unit 50 can now be utilized effectively in various purification stages of the over-all catalyzed methanol carbonylation process or all or part of stream 62 can be purged through stream 64 to reduce the carbonylation catalyst water concentration, if desired.

Again, referring to FIG. 2, at least a portion of the aqueous residue 62 is fed through stream 46 to the decanter 45 by combining the stream 46 with the stream 44, the residue from column 40. Alternatively, the stream 46 can be led directly into decanter 45 at a point in the side of the decanter most advantageous to cause effective separation of the phases in the decanter. Alternatively the water from stream 62 is removed from the system as pure water in stream 64.

An advantage of adding process water from the drying column into the decanter instead of extraneous water is to minimize the amount of water that must eventually be removed from the reaction system. Just as importantly, the aqueous residue stream 62 can be purged from the carbonylation system so as to control and reduce any excess amount of water circulating throughout the carbonylation process. As shown in FIG. 2, the aqueous bottoms stream 62 can be purged as through line 64. Importantly, purge stream 64 is substantially pure water and there is very little acetic acid product which is being discarded. Thus, by utilizing the aqueous phase from the drying column overhead 26 for use in the purification stream, and providing a substantially pure water stream which can be purged without discarding valuable reactants or product, water management of the carbonylation process for converting methanol, methyl acetate or dimethyl ether to acetic acid can be better controlled. This is of particular importance as the water content in the carbonylation reactor is to be minimized so as to increase acetic acid production. When water levels in the carbonylation reactor 10 are to be maintained below 12 wt. % and, more importantly, below 5 wt. %, the water management system that the catalytic distillation unit 50 provides becomes a beneficial part of the over-all carbonylation process.

While the aqueous residue stream 62 has been described with respect to the removal of alkanes from the splitter column overhead, and, in particular, from the heavy methyl iodide-containing phase from splitter column overhead 20, it is to be understood that the aqueous residue 62 can be utilized in other purification processes which have been developed to improve product quality in the carbonylation of methanol, methyl acetate or dimethyl ether to acetic acid. One such process involves the removal of carbonyl compounds from the heavy phase as described in EPO Application No. 487,284 and commonly assigned copending application (our reference: C-7146). In each of these processes, an amine salt is added to the heavy phase to react with the carbonyl compounds to form oximes. The addition of water aids in solvating the oximes into the aqueous phase for separation from the lower boiling organic materials which can be returned to the carbonylation process.

Further, while the acetic acid-containing aqueous stream to be treated is disclosed above as being obtained from the overhead of the drying column and light phase from the splitter, there are other acetic acid-containing aqueous streams formed during the carbonylation process which may be treated in accordance with the catalytic distillation process of this invention. In all cases the process of the present invention is useful to recover the acetic acid from the aqueous streams as methyl acetate, to reduce the energy costs involved in separating the acetic acid from water, and to yield a purer aqueous stream which can be used to control water content throughout the carbonylation process. Those of ordinary skill in this art are well aware of the formation of such streams during the separation and purification of acetic acid from carbonylation reaction to form a substantially dry acetic acid product. Thus, it is contemplated that any aqueous stream formed during the catalyzed carbonylation of methanol, methyl acetate and dimethyl ether to acetic acid or during purification thereof and containing up to 50 wt. % acetic acid can be treated by the catalytic distillation process set forth above. purification thereof and containing up to 50 wt. % acetic acid can be treated by the catalytic distillation process set forth above.

COMPARATIVE EXAMPLE 1

The residue from an alkane stripping column, operated in the manner of price of an acetic acid manufacturing plant operating according to the method of U.S. Pat. No. 5,001,259, was allowed to separate into two phases. The phases were analyzed for composition which was expressed as weight per cent unless otherwise noted in Table I.

TABLE I

| Component | Upper | Lower | Combined Composition |
|---|---|---|---|
| Alkanes | 90.8 | 11.0 | 43.0 |
| Acetic Acid | 9.0 | 88.4 | 56.6 |
| Propionic Acid | 0.05 | 0.1 | 0.1 |
| Water | 0.05 | 0.3 | 0.2 |
| Other | 0.1 | 0.2 | 0.2 |
| Total Iodides, ppm | 1480 | 430 | 850 |

EXAMPLE 1

A sample of the same material as above was mixed well with an equal volume of water and allowed to separate into layers. The layers were analyzed for composition which was expressed as weight per cent except as noted in Table II.

TABLE II

| Component | Upper | Lower | Combined Composition |
|---|---|---|---|
| Alkanes | 98.5 | 0.1 | 45.4 |
| Acetic Acid | 0.4 | 46.5 | 53.6 |
| Propionic Acid | 0.02 | 0.2 | 0.4 |
| Water | <0.5 | 53.0 | 0.3 |
| Others | 0.2 | 0.2 | 0.3 |
| Total Iodides, ppm | 2020 | <10 | 930 |

COMPARATIVE EXAMPLE 2 OPERATION ACCORDING TO THE PRIOR ART

Samples were obtained from a commercial acetic acid plant operated in a manner described by Price in U.S. Pat.

No. 4,102,922, the feed stream and residue from the stripping operation were analyzed. The results were as follows: (All numbers are as wt. % unless otherwise noted as ppm in Table III).

TABLE III

| Component | Feed | Residue |
|---|---|---|
| Methyl iodide | 82.4 | 0.61 (as MeI + MeOAc) |
| Methyl acetate | 9.7 | |
| Acetaldehyde | 0.210 | 5.6 ppm. |
| Methanol | 0.170 | 54 ppm. |
| Butyraldehyde | 0.038 | 62 ppm. |
| Ethyl Iodide | 0.250 | 143 ppm. |
| 2-Ethyl Crotonaldehyde | <10 ppm. | 7.1 ppm. |

EXAMPLE 2 REFLUXING OPERATION OF COLUMN 40

A simulation of Column 40 was operated in the following manner using the same feed material as in Comparative Example 2:

| | |
|---|---|
| Reflux ratio: | 2 |
| Overhead to feed ratio: | 0.93 |
| Pressure: | 1 Atm. |
| Temperature: | 102.3° C. at the bottom |
| | 41.4° C. at the top |

The feed, overhead, and residue were analyzed and the results shown in Table IV. (All components were wt. % unless otherwise noted).

TABLE IV

| Component | Feed | Overhead | Residue |
|---|---|---|---|
| Methyl iodide | 82.4 | 90.4 | <200 ppm (as MeI + MeOAc) |
| Methyl acetate | 9.7 | 8.9 | — |
| Acetaldehyde | 0.210 | 0.195 | — |
| Methanol | 0.170 | 0.190 | — |
| Butyraldehyde | 0.038 | N.D. | — |
| Ethyl iodide | 0.250 | <100 ppm | 3.7 |
| Crotonaldehyde | 7 ppm | N.D. | — |
| Alkanes | 2.0 | 100 ppm | 21.2 |
| Water | 0.4 | 0.08 | 0.12 |
| 2-Ethyl Crotonaldehyde | <10 ppm | N.D. | — |

N.D. none detected

EXAMPLE 3

In this Example, the catalytic distillation of an aqueous stream containing minor amounts of acetic acid was performed utilizing a 2 in. laboratory column containing a fixed bed of Amberlyst 36®, a macroporous sulfonic acid resin catalyst from Rohm and Haas. The column consisted of three sections: a bottom stripping section containing 20 trays, a catalytic section containing the fixed bed of catalyst and an upper rectification section containing 10 trays. The feed to the column comprised an aqueous stream containing 20 wt. % acetic acid which was directed to the top of the fixed bed of catalyst. Directed to the column directly below the fixed bed of catalyst was a stream containing 100% methanol. The molar ratio of methanol to acetic acid was 4.3. The distillate from the column was refluxed at an R/D ratio of 1.5. The column was operated at atmospheric pressure and a temperature at the top of the column of 64° C. and 103° C. at the bottom. The feed rate of the aqueous acetic acid stream and methanol stream to the catalytic distillation column was 14.1 and 6.55 g/min, respectively.

The catalytic distillation achieved 98.9% acetic acid recovery as methyl acetate. The distillate had a composition as follows: 35.6% methyl acetate, 3.2% water and 60.1% methanol (all by weight). The residue stream had a composition as follows: 0.27% acetic acid, 98.3% H$_2$O, <10 ppm methanol, and <10 ppm methyl acetate (all by weight).

EXAMPLE 4

Example 3 was repeated except that the aqueous feed contained 5% acetic acid, the reflux ratio was 1.25, the molar ratio of methanol to acetic acid was 4.3, the column was operated at a temperature of 57 at the top and 103 at the bottom. The feed rate of the aqueous acetic acid was 14.35 g/min and the feed rate of the methanol was 1.64 g/min.

The catalytic distillation achieved 96.7% acetic acid recovery as methyl acetate. The distillate had a composition of 39.1% methyl acetate, 60.4% methanol, 5.4% water, and no acetic acid (all by weight). The residue stream had a composition of 0.152% acetic acid, 99.6% water, <10 ppm methanol, and <10 ppm methyl acetate (all by weight).

EXAMPLE 5

In this Example, the laboratory column described in Example 3 was utilized except that the column above the fixed bed of catalyst did not contain distillation trays such that there was no rectification or reflux in the column above the catalyst. The catalyst again was Amberlyst 36® which was mixed with a laboratory packing. Eight runs were performed in which was varied the amount of acetic acid in the aqueous feed stream, the ratios of methanol to acetic acid and slight variations in the base temperature. The results are shown in Table V. It was found that the higher base temperatures in the column improved removal of the methanol from the residue but also increased the water content of the overhead. The base temperature was varied from 95° to 105° C. The molar ratio of methanol to acetic acid was varied from 2 to 5.6 and the dilute acetic acid feed stream varied with regard to acid concentration from 10.4% to 20.9%.

Of the water that was fed to the column, the percent that went overhead on a mass basis varied from 22–36%. Thus, about 64–88% of the feed water went out of the base while recovering 78–98% of the contained acetic acid content in the distillate as methyl acetate.

TABLE V

| Run No. | Temp. °C. | Feed Rate g/m | | | Mol ratio | Composition of Overhead wt % | | | | Flow rate Overhead g/m | Composition of Residue wt % | | | Flow rate Residue g/m | % conv HAc |
|---|---|---|---|---|---|---|---|---|---|---|---|---|---|---|---|
| | | % HAc | rate | MeOH | MeOH:HAc | HAc | $H_2O$ | MeOH | MeAc | | HAc | $H_2O$ | MeOH | | |
| 1 | 105 | 10.8 | 30.2 | 8.43 | 4.8 | 1.9 | 41.3 | 42 | 16 | 19.67 | 1.2 | 98.7 | 0 | 20.29 | 78 |
| 2 | 101 | 10.4 | 29.0 | 8.95 | 5.6 | 1.8 | 38.8 | 43.6 | 17.7 | 19.14 | 1.3 | 97 | 0.0028 | 21.24 | 91 |
| 3 | 97 | 20 | 17.65 | 8.6 | 4.6 | 2.3 | 30.5 | 45 | 22.8 | 16.65 | 0.7 | 98.1 | 0.58 | 10.27 | 87 |
| 4 | 103 | 20 | 18.48 | 9.2 | 4.6 | 2.5 | 30.2 | 41.4 | 23.2 | 17.13 | 0.8 | 97.8 | 0.099 | 9.65 | 87 |
| 5 | 103 | 20.9 | 29.56 | 7.5 | 2.3 | 3.5 | 35.8 | 29.1 | 34.8 | 19.06 | 2.6 | 93.9 | 0.23 | 19.37 | 87 |
| 6 | 95 | 17 | 40.10 | 8.7 | 2.4 | 4.2 | 34.7 | 22.7 | 40.3 | 20.54 | 5.4 | 91.5 | 4.49 | 30.43 | 98 |
| 7 | 100 | 18.3 | 16.24 | 6.05 | 3.9 | 2.4 | 36.8 | 33.4 | 28 | 12.31 | 0.4 | 96.2 | 0.58 | 9.43 | 94 |
| 8 | 105 | 18.3 | 32.28 | 6.05 | 2 | 3.7 | 39.5 | 17.6 | 39 | 15.07 | 3.2 | 95.8 | 0 | 20.27 | 81 |

HAc = Acetic Acid  MeOH = Methanol  MeAc = Methyl Acetate

What is claimed is:

1. A process for the carbonylation of one or more compounds selected from the group consisting of methanol, dimethyl ether, or methyl acetate to acetic acid comprising;
    carbonylating said methanol, dimethyl ether or methyl acetate in a reaction medium further containing a Group VIII metal carbonylation catalyst, methyl iodide and water to form a reaction product comprising acetic acid and water, separating and purifying said reaction product to substantially dry acetic acid and one or more aqueous streams containing from about 5 to about 30 wt. % acetic acid, the improvement which comprises reacting at least a portion of at least one of the said aqueous streams from the drying column, or the splitter column with methanol in the presence of a second catalyst to form methyl acetate and water, separating the methyl acetate from the water and recycling the methyl acetate to the reactor.

2. The process of claim 1 wherein said second catalyst is an acid catalyst.

3. The process of claim 2 wherein said acid catalyst comprises a cationic exchange resin containing sulfonic acid groups.

4. The process of claim 1 wherein said aqueous stream is reacted by contacting said aqueous stream countercurrently with methanol during contact of said aqueous stream and methanol with said second catalyst.

5. The process of claim 1 wherein at least a portion of the water separated from the methyl acetate is purged.

6. The process of claim 1 wherein said reaction medium contains from a finite amount of water to about 12 wt. % water.

7. The process of claim 6 wherein said reaction medium contains less than 5 wt. % water.

8. The process of claim 1 wherein the acetic acid concentration in the aqueous streams is from about 5 to about 29 wt %.

* * * * *